United States Patent [19]

Dory

[11] Patent Number: 4,561,862
[45] Date of Patent: Dec. 31, 1985

[54] USE OF SELECTED BETA-NITROALKENES AS CETANE NUMBER BOOSTERS FOR DIESEL FUEL

[75] Inventor: Thomas S. Dory, New Haven, Conn.

[73] Assignee: Olin Corporation, Cheshire, Conn.

[21] Appl. No.: 721,099

[22] Filed: Apr. 8, 1985

[51] Int. Cl.[4] .................................................. C10L 1/22
[52] U.S. Cl. ............................................ 44/57; 44/53; 44/72
[58] Field of Search .......................... 44/57, 53, 56, 72

[56] References Cited

U.S. PATENT DOCUMENTS

| | | | |
|---|---|---|---|
| 1,820,983 | 9/1931 | Loomis | 44/57 |
| 2,240,558 | 5/1941 | Ellis | 44/9 |
| 2,274,629 | 2/1942 | Ellis | 44/9 |
| 2,387,279 | 10/1945 | McCracken | 44/57 |
| 2,387,403 | 10/1945 | McCracken | 44/57 |
| 2,392,611 | 1/1946 | Nygaard et al. | 44/57 |
| 2,560,904 | 7/1951 | Sugimoto | 44/57 |
| 2,857,253 | 10/1958 | Hinkamp et al. | 44/62 |
| 3,000,971 | 9/1961 | Frankel et al. | 260/644 |
| 3,001,857 | 9/1961 | Pollock | 44/57 |
| 3,002,827 | 10/1961 | Fenske | 44/72 |
| 3,044,864 | 7/1962 | Ryder | 44/63 |
| 3,380,815 | 4/1968 | Herbst | 44/57 |
| 3,437,693 | 4/1969 | Frump | 252/51.5 R |
| 3,578,687 | 5/1971 | Larkin | 44/72 |
| 3,853,944 | 12/1974 | Cummings | 44/72 |
| 4,073,626 | 2/1978 | Simmons | 44/57 |
| 4,113,444 | 9/1978 | Bunting et al. | 44/72 |
| 4,280,819 | 7/1981 | Hartle et al. | 44/64 |
| 4,328,005 | 5/1982 | Frankel et al. | 44/57 |
| 4,405,333 | 9/1983 | Seemuth | 44/53 |
| 4,417,903 | 11/1983 | Hinkamp | 44/53 |
| 4,424,063 | 1/1984 | Hart | 44/72 |
| 4,448,587 | 5/1984 | Hinkamp et al. | 44/57 |
| 4,473,378 | 9/1984 | Hanlon et al. | 44/57 |

OTHER PUBLICATIONS

Azerb. Neft. Khoz., 1969, 48, 39; Chem. Abstr., 1969, 71, 12683m.

Primary Examiner—William R. Dixon, Jr.
Assistant Examiner—Margareet B. Medley
Attorney, Agent, or Firm—William A. Simons; Thomas P. O'Day

[57] ABSTRACT

Disclosed is a diesel fuel comprising a base fuel selected from the group consisting of liquid hydrocarbons of the diesel boiling range, alcohols, and mixtures thereof, and an effective cetane number-increasing amount of at least one beta-nitroalkene of the formula:

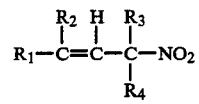

wherein $R_1$, $R_2$, $R_3$ and $R_4$ are individually selected from the group consisting of hydrogen and alkyl groups having from 1 to about 13 carbon atoms, with the proviso that the sum of $R_1$, $R_2$, $R_3$ and $R_4$ contains from 2 to about 13 carbon atoms.

10 Claims, No Drawings

USE OF SELECTED BETA-NITROALKENES AS CETANE NUMBER BOOSTERS FOR DIESEL FUEL

BACKGROUND OF THE INVENTION

1. Field of the Invention

The present invention relates to the use of selected beta-nitroalkenes as cetane number boosters for diesel fuel.

2. Description of the Prior Art

It is known to add small amounts of certain chemicals to diesel fuel to decrease ignition delay and as a result, increase the cetane number of the fuel. These cetane boosters include nitro-parrafin compounds such as nitroethane and nitropentane and alkyl nitrite compounds such as isopropyl nitrite, butyl nitrite and ethyl nitrite (See U.S. Pat. No. 1,820,983); nitric acid, sodium nitrate, or oxides of nitrogen, or mixtures of nitric acid and sulfuric acid (See U.S. Pat. No. 2,240,558); gem dinitro alkanes and cycloalkanes (See U.S. Pat. Nos. 2,387,279; 2,387,403; and 2,560,904); alkyl nitrates such as amyl nitrates (See U.S. Pat. No. 2,857,253); trinitroalkanes such as 2,2,3-trinitrobutane (See U.S. Pat. No. 3,000,971); and gem dinitroalkanoates such as methyl 4,4-dinitropentanoate (See U.S. Pat. No. 3,380,815). U.S. Pat. No. 4,073,623 teaches incorporating into diesel fuel a mixture of an iron salt of an aromatic nitro acid and a nitroaliphatic compound having one to four carbon atoms (cited compounds include nitromethane, nitroethane, nitropropanes and nitrobutanes) in order to reduce air pollutants to lower hard carbon deposits in diesel engines and to prevent or retard slime deposits in the diesel fuel.

With the continued increase in demand for diesel fuel in both passenger cars and trucks and the economic constraints on the quality of available diesel fuel, there is still a need for new and more economical cetane boosters. Accordingly, one object of the present invention is to provide new and more economical cetane boosters.

Another object is to offer a method to improve good grades of diesel fuel and also increase the range of usefulness by raising the cetane number of lower grade fuels to a point where they can be used.

BRIEF SUMMARY OF THE INVENTION

The present invention, therefore, is directed to a method for increasing the cetane number of a diesel fuel comprising a base fuel selected from the group consisting of liquid hydrocarbons of the diesel boiling range, alcohols, and mixtures thereof; said method comprising:

incorporating in said base fuel an effective cetane number-increasing amount of at least one beta-nitroalkene of the formula:

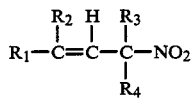

wherein $R_1$, $R_2$, $R_3$ and $R_4$ are individually selected from the group consisting of hydrogen and alkyl groups having from 1 to about 13 carbon atoms, with the proviso that the sum of $R_1$, $R_2$, $R_3$ and $R_4$ contains from 2 to about 13 carbon atoms.

The present invention furthermore is directed to a diesel fuel comprising:

a base fuel selected from the group consisting of liquid hydrocarbons of the diesel boiling range, alcohols, and mixtures thereof, and an effective cetane number-increasing amount of at least one beta-nitroalkene of the formula:

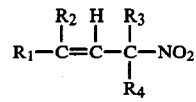

wherein $R_1$, $R_2$, $R_3$ and $R_4$ are individually selected from the group consisting of hydrogen and alkyl groups having from 1 to about 13 carbon atoms, with the proviso that the sum of $R_1$, $R_2$, $R_3$ and $R_4$ contains from 2 to about 13 carbon atoms.

DETAILED DESCRIPTION

Beta-nitroalkenes may be prepared by reacting the corresponding bromides or chlorides with sodium or silver nitrate [Organic Synthesis, 1958, 38, 75; J. Org. Chem., 1978, 43, 3116] or with $N_2O_4$ [Zh. Organ. Khim., 1965, 1, 236; Chem. Abstr., 1965, 62, 16034h]. Another method of making beta-nitroalkenes involves the reaction of the corresponding alpha-olefin with concentrated nitric acid [Doklady Akad. Nauk SSSR, 1951, 77, 1031; Chem. Abstr. 1952, 46, 419d].

Preferred beta-nitroalkenes include those, subject to the above proviso, where $R_1$ is an alkyl group having 3 to about 9 carbon atoms and $R_2$, $R_3$ and $R_4$ are individually selected from hydrogen and lower alkyl groups having 1 to 4 carbon atoms.

More preferred beta-nitroalkenes include those where $R_1$ is an alkyl group having 3 to about 6 carbon atoms and $R_2$, $R_3$ and $R_4$ are individually selected from hydrogen, methyl and ethyl groups.

Representative beta-nitroalkenes include the following:

1-nitro-2-hexene
1-nitro-2-octene
3-methyl-1-nitro-2-pentene
3-methyl-1-nitro-2-hexene
3-ethyl-1-nitro-2-pentene
1-nitro-2-dodecene
3-methyl-1-nitro-2-butene
3-ethyl-1-nitro-2-hexene
3-methyl-1-nitro-2-octene
3-methyl-1-nitro-2-decene
3-methyl-1-nitro-2-dodecene
3-propyl-1-nitro-2-hexene
1-methyl-1-nitro-2-hexene
3,4-dimethyl-1-nitro-2-pentene
3,4-dimethyl-1-nitro-2-hexene One or more cetane boosters of the present invention may be employed in the diesel fuel at various concentrations depending upon many factors including the particular type of diesel fuel employed (e.g. its initial cetane value), specific cetane booster employed, other ingredients in the fuel formulation and the particular use for the fuel (e.g. cetane number desired). Alcohol fuels such as methanol, ethanol, isopropanol, isobutanol, hexanol and the like have very low cetane values and large amounts of cetane boosters are required. Thus, strictly alcohol diesel fuels may require about 5% to about 25% by weight incorporation of these cetane boosters.

Blends of alcohol and petroleum derived diesel fuel have higher cetane values and require less cetane booster. A useful range is about 0.5–10 weight percent.

Petroleum derived distillate fuels in the diesel boiling range require only small amounts of cetane booster to achieve a significant increase in cetane number. Such fuels without any cetane booster generally have cetane numbers in the range of about 25–60. Cetane numbers in the range of 25–35 are considered low and those in the range of 50–60 are considered top grade diesel fuel. Diesel fuels in the 35–50 mid-range are most common. An object of this invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additives. Accordingly, a useful concentration range in petroleum derived diesel fuel is about 0.01–5.0 weight percent and preferably about 0.05–1.0 weight percent.

The following Examples and Comparisons are given to further illustrate the present invention. All parts and percentages are by weight unless stated otherwise.

EXAMPLE 1

Synthesis of 1-Nitro-2-hexene

1-Hexene (125 mL, 1.0 mole) and concentrated nitric acid (90 mL, 2.0 moles) were mixed at room temperature. With rapid stirring the solution was heated to 40° C. for 4½ hours. With continued stirring the solution was cooled to room temperature and the organic layer separated. It was washed with a saturated sodium chloride solution then dried over magnesium sulfate. After filtering, vacuum distillation removed unreacted 1-hexene leaving one product, 1-nitro-2-hexene in 20.5% yield. This desired product was confirmed by IR and gas chromatography (GC) analysis.

EXAMPLE 2

Synthesis of 1-Nitro-2-octene

1-Octene (159 mL, 1.0 mole) and concentrated nitric acid (71 mL, 1.5 moles) were mixed together at room temperature. With rapid stirring the solution was heated to 90° C. for 2 hours. Heat was removed and stirring continued an additional 30 min. The organic layer was separated and washed with a saturated sodium chloride solution (3×75 mL), then dried over magnesium sulfate. After filtration, unreacted 1-octene was removed by vacuum distillation (0.5 Torr, 28° C.) leaving the product as an orange oil in 38.4% yield. Gas chromatography of this product indicated it was a mixture of cis- and trans-1-nitro-2-octene and a small amount of another nitrated compound, probably 1-nitro-2-octanol. These structures were confirmed by IR and NMR analysis.

EXAMPLE 3

Two Syntheses of 3-methyl-1-nitro-2-pentene (A) By addition of nitric acid to 3-methyl-1-pentene. 3-Methyl-1-pentene (15 mL, 0.12 moles) and concentrated nitric acid (15 mL, 0.24 moles) were mixed together at room temperature then with rapid stirring heated to 48° C. for 30 min. After cooling to room temperature with stirring, the organic layer was separated and washed with a saturated sodium chloride solution (3×10 mL). After drying over magnesium sulfate and filtering, vacuum distillation (0.5 torr, 25° C.) removed unreacted 3-methyl-1-pentene. The orange product distilled at 0.5 Torr, 38° C. in 75.6% yield. This product was confirmed by IR and GC analysis.

(B) By addition of silver nitrite to 1-bromo-3-methyl-2-pentene. 1-Bromo-3-methyl-2-pentene was made by addition of phosphorus tribromide to 3-methyl-2-pentene-1-ol at 0° C. A flask was charged with ether (250 mL) and silver nitrite (15.4 g, 0.10 mole) then covered to keep out light. The solution was cooled to 5° C. and 1-bromo-3-methyl-2-pentene was slowly added with stirring. After 16 hours the solution was warmed to room temperature and stirred an additional 6 hours. The silver salts were removed by filtration and 1 mL methyl alcohol was added to the ether solution. After 8 hours the solvents were removed by vacuum leaving 3-methyl-1-nitro-2-pentene as an orange oil in 78% yield. This product was confirmed by IR and GC analysis.

EXAMPLE 4

Synthesis of 3-Methyl-1-nitro-2-hexene

3-Methyl-1-hexene (22.2 mL, 0.15 moles) was mixed with concentrated nitric acid (18 mL, 0.28 moles) at room temperature. With rapid stirring the solution was heated to 65° C. for 3 hours. The heat was removed and the solution stirred an additional 30 min. The organic layer was separated and washed with a saturated sodium chloride solution (3×15 mL) then dried over magnesium sulfate. Vacuum distillation (20 Torr, 28° C.) removed unreacted 3-methyl-1-hexene. A yellow oil remained. Gas chromatography and IR spectroscopy indicate both cis- and trans-3-methyl-1-nitro-2-hexene are present along with a small amount of 1-nitro-2-hexanol. These structures were confirmed by IR and GC analysis.

EXAMPLE 5

Synthesis of 3-Ethyl-1-nitro-2-pentene

3-Ethyl-1-pentene (15 mL, 0.11 moles) and concentrated nitric acid (9.6 mL, 0.15 moles) were mixed together at room temperature then with rapid stirring, heated to 70° C. for 4 hours. Heat was removed and stirring continued an additional 30 min. The organic layer was separated and washed with a saturated sodium chloride solution (3×15 mL) then dried over magnesium sulfate. After filtering, vacuum distillation (20 Torr, 28° C.) removed unreacted 3-ethyl-1-pentene. The remaining yellow oil contains 3-ethyl-1-nitro-2-pentene (12% yield) and a small amount of 3-ethyl-2-pentylnitrate. This was confirmed by IR and GC analysis.

EXAMPLE 6

Synthesis of 1-Nitro-2-dodecene

1-Dodecene (222 mL, 1.0 mole) and concentrated nitric acid (96 mL, 1.5 moles) were mixed together at room temperature. The solution was heated to 100° C. for 4 hours with rapid stirring then cooled to room temperature. The organic layer separated and washed with a saturated sodium chloride solution (3×75 mL). After drying over magnesium sulfate and filtering, the orange oil was vacuum distilled (0.5 Torr, 36° C.) which removed unreacted 1-dodecene. The remaining orange/red oil is a mixture containing 1-nitro-2-dodecene and 1-nitro-2-dodecanol. This oil was further reacted with methanesulfonyl chloride and triethylamine to dehydrate the alcohol and produce more 1-nitro-2-dodecene. After this dehydration step, the structure of 1-nitro-2-dodecene was confirmed by IR and GC analysis.

EXAMPLE 7

Synthesis of 3-Methyl-1-nitro-2-butene

To a solution containing dimethylsulfoxide (300 mL) and sodium nitrite (24.2 g, 0.35 moles) 1-bromo-3-methyl-2-butene was added dropwise with stirring. After two hours the stirred solution was poured into an ice water/petroleum ether (300/100 mL) mixture. The petroleum ether fraction was separated. The aqueous fraction was washed three times with small portions of fresh petroleum ether. The washings were combined with the original petroleum ether extract, then dried over magnesium sulfate. After filtering the petroleum ether was removed under mild vacuum. The remaining yellow oil was then vacuumed distilled. The product distilled as a light yellow oil (45 Torr, 34° C.) in 35% yield. The product was confirmed as 3-methyl-1-nitro-2-butene by NMR, IR and gas chromatography analysis.

The following Comparison examples were carried out to further illustrate the superior results associated with the above Examples of the present invention. As shown in these Comparisons, nitroalkenes which do not have both a nitro group beta to the olefinic carbon bond and from 5 to 16 carbon atoms provide very low cetane increase to diesel fuel or are unstable for use therein, or both. The instability is believed to be caused by their low boiling points which render them unsuitable for use at the high operating temperatures of diesel fuels. This instability may also be caused by the structural transformation into other isomers and high temperature decomposition as observed during gas chromatograph analysis.

COMPARISON 1

Synthesis of 2-Methyl-1-nitropropene

1-Nitro-2-methyl-2-propanol (4.77 g, 0.04 moles) in methylene chloride (40 mL) under a nitrogen atmosphere was dehydrated using methanesulfonyl chloride (3.1 mL, 0.04 moles) and triethylamine (22.0 mL, 0.16 moles) at 0° C. The solution was stirred for 20 min. subsequent to triethylamine addition. The solution was washed with water, 5% aqueous hydrochloric acid and a saturated sodium chloride solution. Solvent was removed by vacuum leaving an orange oil. Vacuum distillation (25° C., 0.5 Torr) produced 2.3 g, 55% yield of the product as a light yellow oil. This structure was confirmed by IR, GC and NMR analysis. When the product was injected into the gas chromatograph machine for analysis, decomposition products were observed. This is believed to be caused by the high temperatures associated with the injection port of the G.C. (i.e. about 200° C.) instrument.

COMPARISON 2

Synthesis of 2-Nitro-2-butene

3-Nitro-2-butanol (8.6 mL, 0.08 moles) in methylene chloride (80 mL) under a nitrogen atmosphere was dehydrated by the addition of methanesulfonyl chloride (6.19 mL, 0.08 moles) and triethylamine (44.5 mL, 0.32 moles) at 0° C. The solution was stirred for 15 min. at 0° C. subsequent to triethylamine addition.

The reaction mixture was washed with water, 5% aqueous hydrochloric acid and saturated sodium chloride solution. The methylene chloride solution was dried over magnesium sulfate then filtered. Solvent was removed by vacuum leaving a deep orange oil. Vacuum distillation (30° C., 0.5 Torr) produced the product as a light yellow oil, 3.7 g. 45.7% yield. This structure was confirmed by IR, GC and NMR analysis.

COMPARISON 3

Synthesis of 1-Nitro-2-methyl-1-butene

A flask was charged with nitromethane (100 mL, 1.85 moles), methyl ethyl ketone (100 mL, 1.12 moles) with piperidine (8.0 mL, 0.08 moles). The solution was stirred for 72 hrs. at room temperature. Vacuum distillation (30° C., 11 Torr) removed unreacted methyl ethyl ketone and nitromethane. The product distilled at 102° C., 11 Torr as a yellow orange oil, 5.1 g, 46% yield. This structure was confirmed by IR and GC analysis.

COMPARISON 4

Synthesis of 1-Nitropropene

1-Nitro-2-propanol (82.0 g, 0.78 moles) in methylene chloride (100 mL) under an argon atmosphere was dehydrated using methanesulfonyl chloride (60.4 mL, 0.78 moles) and triethylamine (278.8 mL, 2.0 moles) at 0° C. The solution was stirred for 20 min. subsequent to triethylamine addition. The solution was washed with water, 5% aqueous hydrochloric acid and a saturated sodium chloride solution. The solvent was removed under a mild vacuum leaving the dark orange crude product. Vacuum distillation (35° C., 0.1 Torr) produced the product as a light yellow oil. This structure was confirmed by IR, GC and NMR analysis.

COMPARISON 5

Synthesis of 2,4-Dimethyl-1-nitro-1-pentene 2,5-Dimethyl-1-nitro-2-pentanol (135 mL, 0.75 moles) in methylene chloride (150 mL) under an argon atmosphere was dehydrated using methanesulfonyl chloride (58.1 mL, 0.75 moles) and triethylamine (209 mL, 1.5 moles) at 0° C. Methanesulfonyl chloride was added dropwise to the pentanol/triethylamine solution followed by an additional 30 min. of stirring. The reaction solution was washed with water, 5% aqueous hydrochloric acid and a saturated sodium chloride solution then dried over magnesium sulfate. The solvent was removed by vacuum leaving an orange oil. The structure of 2,4-dimethyl-1-nitro-pentene was confirmed by IR and GC analysis.

COMPARISON 6

Synthesis of 4-Propyl-3-nitro-3-heptene

3-Ethyl-4-nitro-3-hexanol (140 mL, 0.84 moles) in methylene chloride (100 mL) under an argon atmosphere was dehydrated using methanesulfonyl chloride (65 mL, 0.84 moles) and triethylamine (234 mL, 1.68 moles) at 0° C. Methanesulfonyl chloride was added dropwise to the hexanol/triethylamine chloride solution followed by an additional 30 min. of stirring. The reaction solution was washed with water, 5% aqueous hydrochloric acid and a saturated sodium chloride solution then dried over magnesium sulfate. Solvent was removed in a mild vacuum leaving an orange oil. The structure of the title compound was confirmed by IR, GC and NMR analysis.

TESTING OF CETANE NUMBER

The base fuel oil was a Number 2 diesel fuel oil, supplied by the Phillips Chemical Company, having the following typical analysis:

| Gravity, °API | 35.2 |
|---|---|
| Distillation Range, °F. | |
| IBP | 375 |
| 10% point | 431 |
| 50% point | 505 |
| 90% point | 598 |
| End point | 653 |
| Flash Point (PM), °F. | 162 |
| Kinematic Viscosity, cs | 2.52 |
| Cetane Number | 47.8 |

This cetane number for this base fuel was determined in a cetane rating engine according to ASTM D-613. The compounds of Examples 1–7 and Comparisons 1–6 were added to individual samples of the base fuel at one percent (1%) by weight concentration. The cetane numbers of the blends containing the compounds of Examples 1, 2, 3B and 6 were determined according to the same method (ASTM D-613) used for determining the cetane number of the base fuel. The cetane number of the blends containing the compounds of Examples 4, 5 and 7 and Comparisons 1–6 were determined using a Foxboro Octane Analyzer (Model 81-LM1) made by the Foxboro Company of Houston, Texas, modified to determine cetane numbers. In carrying out these tests, standard ASTM reference fuels T-17 and U-10 (supplied by Phillips Chemical Company) were employed.

The testing on the cetane rating engine was done strictly in accordance to ASTM Method D-613. The testing on the modified Foxboro Octane Analyzer was done by slightly modifying the ASTM D-613 method. A reference fuel was injected initially. This was followed by injection of the blend being tested. The cetane number of this blend was then determined from a predetermined calibration curve obtained using blends of ASTM fuels T-17 and U-10. Duplicate samples of each blend were used to determine the final cetane number given in Table I, below.

TABLE I

| Example or Comparison | Additive (1% Wt.) | Final Cetane Number of Blend | Cetane Number Difference Over Base Fuel |
|---|---|---|---|
| E-1 | 1-Nitro-2-Hexene | 58.7 | 10.9 |
| E-2 | 1-Nitro-2-Octene | 56.7 | 8.9 |
| E-3B | 3-Methyl-1-Nitro-2-Pentene | 54.5 | 6.7 |
| E-4 | 3-Methyl-1-Nitro-2-Hexene | 50.9 | 3.1 |
| E-5 | 3-Ethyl-1-Nitro-2-Pentene | 51.0 | 3.2 |
| E-6 | 1-Nitro-2-Dodecene | 51.1 | 3.3 |
| E-7 | 3-Methyl-1-Nitro-2-Butene | 56.1 | 8.3 |
| C-1 | 2-Methyl-1-Nitropropene | 55.5 | 7.7 |
| C-2 | 2-Nitro-2-Butene | 48.3 | 0.5 |
| C-3 | 1-Nitro-2-Methyl-1-Butene | 49.4 | 1.6 |
| C-4 | 1-Nitropropene | 48.2 | 0.4 |
| C-5 | 2,4-Dimethyl-1-Nitro-1-Pentene | 49.3 | 1.5 |
| C-6 | 4-Propyl-3-Nitro-3-Heptene | 47.8 | 0.0 |

As can be seen from Table I, all of the compounds of Examples 1–7 showed a significant increase in cetane number. In contrast, five out of six compounds in Comparison 1–6 showed a relatively low increase in cetane number. It is believed that the presence of the nitro group beta to the carbon-carbon double bond and the presence of a hydrogen attached to the carbon-carbon double bond on the nitro side is the cause of the significant increase in cetane number. Furthermore, it is believed that having five to sixteen carbon atoms in the compounds provide the desired combination of stability and compatibility in boiling point and solubility with diesel fuel. The compound of Comparison 1, which provided a good increase in cetane number, was found to be unsuitable for use in diesel fuels because of its low boiling point which would cause it to vaporize before the diesel fuel does in operation. Furthermore, this compound tends to not be structurally stable over a period of time (i.e. it tends to either polymerize or isomerize during storage).

What is claimed is:

1. A diesel fuel comprising a base fuel selected from the group consisting of liquid hydrocarbons of the diesel boiling range, alcohols, and mixtures thereof, and an effective cetane number-increasing amount of at least one beta-nitroalkene of the formula:

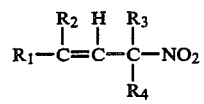

wherein $R_1$, $R_2$, $R_3$ and $R_4$ are individually selected from the group consisting of hydrogen and alkyl groups having from 1 to about 13 carbon atoms, with the proviso that the sum of $R_1$, $R_2$, $R_3$ and $R_4$ contains from 2 to about 13 carbon atoms.

2. The diesel fuel of claim 1 wherein, subject to said proviso, $R_1$ is an alkyl group having 3 to about 9 carbon atoms and $R_2$, $R_3$ and $R_4$ are individually selected from hydrogen and lower alkyl groups having 1 to 4 carbon atoms.

3. The diesel fuel of claim 1 wherein $R_1$ is an alkyl group of 3 to about 6 carbon atoms and $R_2$, $R_3$ and $R_4$ are individually selected from hydrogen, methyl and ethyl groups.

4. The diesel fuel of claim 1 wherein said beta-nitroalkene is 1-nitro-2-hexene.

5. The diesel fuel of claim 1 wherein said beta-nitroalkene is 1-nitro-2-octene.

6. A method for increasing the cetane number of a diesel fuel comprising a base fuel selected from the group consisting of liquid hydrocarbons of the diesel boiling range, alcohols, and mixtures thereof; said method comprising:
incorporating into said base fuel an effective cetane number-increasing amount of at least one beta-nitroalkene of the formula:

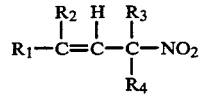

wherein $R_1$, $R_2$, $R_3$ and $R_4$ are individually selected from the group consisting of hydrogen and alkyl groups having from 1 to about 13 carbon atoms, with the proviso that the sum of $R_1$, $R_2$, $R_3$ and $R_4$ contains from 2 to about 13 carbon atoms.

7. The method of claim 6 wherein, subject to said proviso, $R_1$ is an alkyl group having 3 to about 9 carbon atoms and $R_2$, $R_3$ and $R_4$ are individually selected from hydrogen and lower alkyl groups having 1 to 4 carbon atoms.

8. The method of claim 6 wherein $R_1$ is an alkyl group of 3 to about 6 carbon atoms and $R_2$, $R_3$ and $R_4$ are individually selected from hydrogen, methyl and ethyl groups.

9. The method of claim 6 wherein said beta-nitroalkene is 1-nitro-6-hexene.

10. The method of claim 6 wherein said beta-nitroalkene is 1-nitro-2-octene.

* * * * *